United States Patent [19]
Mann et al.

[11] Patent Number: 5,127,402
[45] Date of Patent: Jul. 7, 1992

[54] SYSTEM AND METHOD FOR MAINTAINING STIMULATION PULSE AMPLITUDE AT BATTERY DEPLETION BY SELF-REGULATING CURRENT DRAIN USAGE

[75] Inventors: Brian M. Mann, Beverly Hills; John W. Poore, South Pasadena, both of Calif.

[73] Assignee: Siemens Pacesetter, Inc., Sylmar, Calif.

[21] Appl. No.: 691,928

[22] Filed: Apr. 26, 1991

Related U.S. Application Data

[63] Continuation of Ser. No. 448,191, Dec. 7, 1989, Pat. No. 5,031,616.

[51] Int. Cl.⁵ .................................. A61N 1/362
[52] U.S. Cl. .................................. 128/419 PT
[58] Field of Search ............ 128/419 PG, 419 PS, 128/419 PT

[56] References Cited

U.S. PATENT DOCUMENTS

| | | | |
|---|---|---|---|
| 3,901,247 | 8/1975 | Walmsley | 128/419 PG |
| 4,095,603 | 6/1978 | Davies | 128/419 PT |
| 4,120,306 | 10/1978 | Renire | 128/419 PT |
| 4,197,850 | 4/1980 | Schulman et al. | 128/419 PG |
| 4,313,442 | 2/1982 | Knodson et al. | 128/419 PG |
| 4,324,252 | 4/1982 | Rossing et al. | 128/419 PG |
| 4,390,020 | 6/1983 | Herpers | 128/419 PG |
| 4,416,282 | 11/1983 | Saulson et al. | 128/419 PG |

Primary Examiner—William E. Kamm
Attorney, Agent, or Firm—Leslie S. Miller; Bryant R. Gold

[57] ABSTRACT

A system within an implantable stimulation device and a method for limiting the extent to which any high power consumption modes, such as a rate response mode, can be utilized during low battery periods. A battery threshold detector is utilized to detect when the battery is below a predetermined threshold. The implantable stimulation device then switches from a high current drain mode of operation to progressively lower current drain modes of operation. This configuration allows a significant reduction in current drain at RRT and further prevents the output amplitude from dropping below the capture level and prevents the remaining battery capacity from being rapidly used up.

22 Claims, 5 Drawing Sheets

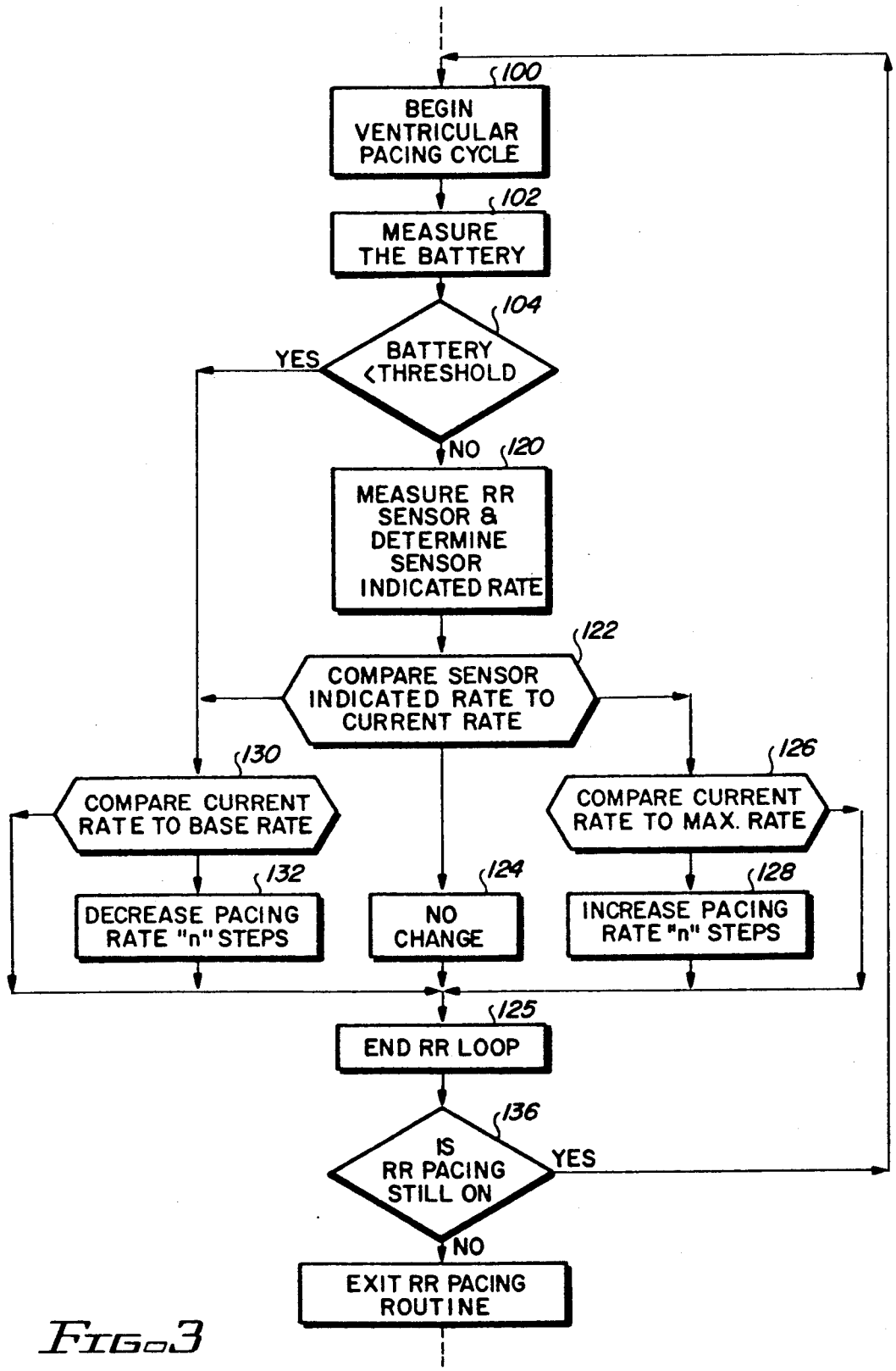

SYSTEM AND METHOD FOR MAINTAINING STIMULATION PULSE AMPLITUDE AT BATTERY DEPLETION BY SELF-REGULATING CURRENT DRAIN USAGE

This application is a continuation of application Ser. No. 07/448,191, filed on Dec. 7, 1989, now U.S. Pat. No. 4,031,616, issued on Jul. 16, 1991.

BACKGROUND OF THE INVENTION

1. Field of the Invention

The present invention relates generally to implantable cardiac pacemakers, and more specifically to rate-responsive pacemakers wherein the upper rate is limited as the battery approaches its end-of-life (EOL). In alternative embodiments, the invention can be used with any high power consumption features within an implantable device to extend the longevity of the battery by limiting the extent to which these features may be utilized.

Implantable cardiac pacemakers are powered by a battery within the pacemaker housing. Once implanted, it is difficult to determine the battery's state of depletion and, thus, the need for replacement. Although the surgery required for replacement is relatively minor, the associated risks of complications to the patient are ever present. In general, it is considered better to avoid replacement of a properly functioning pacemaker until absolutely necessary.

To determine when to explant a pacemaker prior to its EOL, physicians plan their follow-up schedules less frequently during the battery's "beginning-of-life" (BOL) and more frequently towards the battery's recommended replacement time (RRT) and the battery's "end-of-life" (EOL). (EOL is defined as the point in time in which the pacemaker pulse amplitude is reduced to approximately 50 percent of the programmed value.) As the basis, physicians estimate the remaining battery capacity by subtracting the "nominal" current drain of the pacemaker, usually specified at 5 volts with 100% pacing at a rate of 70 pulses-per-minute (ppm), from the theoretical available amp-hour capacity of the battery. Even though accurate battery capacity sensors have been developed (see, for example, U.S. Pat. No. 4,556,061 to Barreras et al.), the physician must still accurately predict the power consumption for the remaining period. With sophisticated pacemakers and unpredictable current drain modes of operation, physicians have to schedule more frequent follow-up visits to accurately monitor the replacement time and still avoid premature surgical replacement.

Current drain on a battery is largely dictated by the pacer output amplitude, pulse width, and rate. Programmability of these pacemaker parameters offers some flexibility to safely prolong the longevity of the battery. For example, it is well known that the battery life can be increased anywhere from 3 to 9 months by programming the rate to 70 instead of 90 beats-per-minute (bpm). However, not all patients can tolerate being paced at 70 bpm. Active patients need a higher rate during exercise. In patients with a normal sinus node, higher rates may be achieved with a dual chamber pacemaker, wherein the atrial rate is sensed and the ventricles are stimulated a short delay later (mimicking a normal heart). During exercise, the atrial rate may vary between 70 and 120 bpm or more. It is also known that rate-responsive pacemakers can increase the pacing rate according to an additional sensor (accelerometer or "activity" sensor, oxygen saturation, QT measurements, respiration rate, temperature, etc.). The purpose of such pacemakers is to accelerate the rate when the atrium is incompetent, that is, non-responsive to exercise stress or prone to atrial flutter or fibrillation.

In both of these pacemakers, the amount of current drain on the battery can change quite rapidly as the pacing rate of the pacer may change from a low rate to a high rate. This is especially true where the patient's own intrinsic rhythm is able to sustain the patient's needs at low activity levels (a low current drain condition), but where stimulated pacing is required in one or both chambers of the heart at a high activity level (a high current drain condition). Unfortunately, such large variations in current drain can cause a sudden battery voltage drop below the EOL voltage level such that the possibility exists that the battery voltage could drop low enough to cause loss of capture. Furthermore, if pacing occurs at fast rates, such as occurs during exercise, the increase in current drain could dramatically reduce or even eliminate the safety margin associated with the last reported recommended replacement time (RRT) of the pacer, particularly when the last reported RRT is based on the current drain while the patient was at the rest rate.

It is also known in the art (see for example, U.S. Pat. No. 4,686,988 to Sholder) that battery current drain due to the delivered pacing pulse can be reduced by automatically adjusting the output amplitude and/or pulse width of the pacing pulse such that the lowest possible output is delivered which can still stimulate or "capture" the heart. This feature does ensure that the patient will not lose capture throughout the life of the pacemaker, however, this increase in processing time of the microprocessor and the constant changing of the output amplitude and/or pulse width introduces still more variables to consider when determining the replacement time of the pacemaker.

Furthermore, with the advent of microprocessor-based pacemakers, functionality has been extended to automatic adjustment of pacemaker parameters, storing and telemetering of intracardiac electrograms (EGMs), processing multiple sensors, detecting and breaking arrhythmias and recognizing waveform patterns. The current drain of the pacemaker may also be significantly influenced by the duty cycle of the microprocessor in performing these functions. Without careful monitoring of the battery voltage, these high current drain situations may cause a temporary drop in available battery voltage, increase the risk of loss of capture, and dramatically use up the remaining battery capacity.

What is needed is a pacemaker which can regulate its own current drain usage, conserve the limited battery energy towards EOL, prevent loss of capture by limiting high current drain modes, and ultimately eliminate premature replacement of the pacemaker by eliminating the unpredictable nature of the RRT to EOL interval. Furthermore, this pacemaker should not burden the physician by increasing the number of follow-up visits near EOL.

SUMMARY OF THE INVENTION

The disadvantages and limitations of the background art discussed above are overcome by the present invention. The present invention may be used to limit power consumption as the battery approaches and exceeds the RRT. The present invention is capable of selectively altering operating parameters, based on a predetermined priority, to provide the longest possible active life for the pacemaker, while still providing a good quality of life as required by the patient's physiological needs. These actions help conserve the limited remaining battery energy and prevent loss of capture.

The present invention includes an implantable cardiac device having conventional components including a battery, a pulse generator for generating stimulating pulses, sense amplifiers for sensing cardiac signals, and a timing and control means. The device also includes a battery threshold detector for detecting a predetermined threshold level of the battery, having a high current drain mode of operation and at least two successively lower current drain modes of operation, and a processing means for switching to a successively lower current drain mode each time the battery threshold detector indicates that the battery voltage is below a prescribed threshold. This configuration allows a significant reduction in current drain.

In the preferred embodiment, the implantable cardiac device is a rate-responsive pacemaker. Instead of simply reporting the battery voltage upon interrogation of the pacemaker or completely disabling functions, as is done in the prior art, the pacemaker will automatically regulate its current drain usage by limiting the pacing rate to a value less than the sensor-indicated rate. This is achieved by continuously monitoring the battery voltage for the occurrence of a voltage at or below the predetermined threshold during rate-responsive pacing. If such a voltage is detected, the allowable maximum sensor rate is automatically reduced (which, in turn, reduces the battery current drain). This new allowable maximum sensor rate remains in effect until the battery voltage is above the predetermined threshold or until the allowable maximum sensor rate is otherwise reset. As the battery continues to deplete, the allowable maximum sensor rate will eventually reduce the pacing rate to the programmed rest rate, or "base" rate, effectively disabling rate-responsive pacing. In an alternative embodiment, the rate could even go lower than the rest rate.

In effect, the pacemaker is switching from a high current drain mode (rate-responsive pacing at a high rate), to a lower current drain mode (rate-responsive pacing at successively lower rates) until the battery voltage is above the predetermined threshold. In yet another embodiment, the invention controls the extent to which other high current drain modes can be utilized by the pacemaker once the predetermined threshold has been reached.

The invention described herein further contemplates a method for maintaining output amplitude at battery depletion by self-regulating current drain usage. In one embodiment, this is achieved by reducing the rate of a rate-responsive pacemaker when the battery voltage reaches a predetermined threshold value. In a second embodiment, the pacemaker is switched from a high current drain mode to a successively lower current drain mode until the battery voltage is above the predetermined threshold.

As such, the present invention does not require an increase in physician follow-up as the battery approaches RRT. Rather, its self-regulation of high current drain features allows the same follow-up schedule as VVI pacemakers with an increase in reliability and confidence.

Finally, all of the problems and disadvantages of the prior art are overcome in the present invention without incurring any substantial relative disadvantage. It will therefore be perceived that the advantages of the present invention result in extending the longevity of the pacemaker while providing a high quality of life for the patient for as long as possible, making the method of the present invention a highly desirable enhancement to implantable cardiac pacemaker therapy.

DESCRIPTION OF THE DRAWINGS

The features and other advantages of the present invention may be more readily understood by reference to the following description taken in conjunction with the accompanying drawings, in which:

FIG. 3 is a diagram which teaches the basic principles of the method for maintaining output amplitude at battery depletion in the rate-responsive processor shown in FIG. 2A.

DETAILED DESCRIPTION OF THE PREFERRED EMBODIMENT

Figure 1:
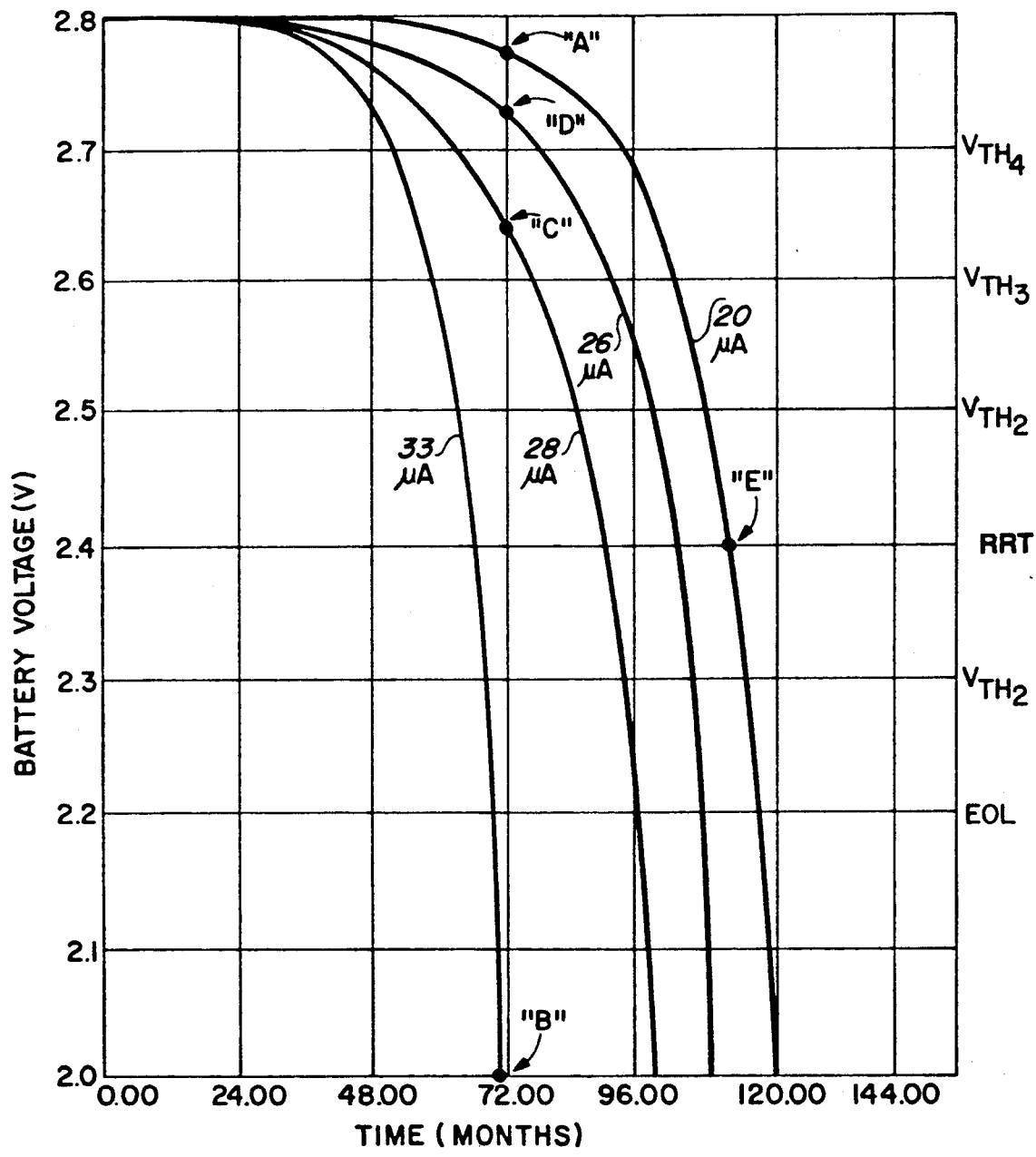
FIG. 1 shows the projected discharge characteristics of a typical lithium iodide battery.

The present invention may easily be understood with reference to FIG. 1 which shows the estimated discharge characteristics of a lithium iodide battery cell as is commonly used in many pacemakers today. These cells may be characterized as a fixed voltage source, with a stable open circuit voltage and an internal impedance which increases over time. Therefore, the available terminal voltage will vary inversely with the current drain from the battery, due to the internal voltage drop across the internal cell impedance.

As mentioned previously, the current drain is significantly influenced by the rate at which the pacemaker is delivering stimulating pulses. Point "A" in FIG. 1 represents a patient with a rate-responsive pacemaker wherein the patient is resting, therefore the current drain is low, say, at 20 uA. If the patient should suddenly need a high increase in rate, the current drain may increase to, say, 33 uA, and the available battery voltage would drop to 2.0 volts as indicated at point "B". It can therefore be seen that this increase in rate can cause a sudden battery voltage drop below the EOL voltage level such that the possibility exists that the battery voltage could drop low enough to cause loss of capture. By limiting the pacing rate such that the current drain was only 28 uA, the available battery voltage would rise to point "C", clearly well above the RRT threshold. A further reduction in the pacing rate, would enable the available battery voltage to rise to point "D" with an even greater safety margin.

It can further be easily seen in FIG. 1 that the remaining time to EOL is significantly increased as the operating point moves from point "B" to points "C", "D", and ultimately to "A". Once the battery terminal voltage reaches RRT at point "E", and the current drain cannot be reduced any further, the pacing rate is set to the Base Rate (or rest rate) and rate-responsive pacing is effectively suspended.

A block diagram of the present invention, coupled to a rate-responsive pacer, is shown in FIG. A. A complete description of the rate-responsive pacemaker is included in U.S. Pat. No. 4,940,053, entitled "Energy Controlled Rate-Responsive Pacemaker Having Automatically Adjustable Control Parameters," and U.S. Pat. No. 4,940,052, entitled "Microprocessor Controlled Rate-Responsive Pacemaker Having Automatic Rate Response Threshold Adjustment." These patents are assigned to the same assignee as is the present application, and these two patents are hereby incorporated herein by reference.

Briefly, the rate-responsive pacemaker functions as follows. The pacemaker 10 includes a conventional pacemaker chip 12 which has a pulse generator 14 for generating stimulating pulses 16 to the heart 30. Sense amplifiers (not shown) are employed to sense cardiac events and to communicate this information to timing and control circuitry 18. The timing and control circuitry 18 controls a base rate signal 20 for the pulse generator 14 and controls the inhibition of a stimulus in the event of a sensed cardiac signal. Telemetry circuits 22 are connected electrically to the timing and control circuitry 18. An external programmer 24 is used to noninvasively send programming signals to the telemetry circuits 22. These programming signals are depicted symbolically as the wavy line 26 in FIG. 2A. It is noted that such signals may be sent bi-directionally between the external programmer 24 and the pacemaker 10. In this way the external programmer 24 can noninvasively alter the pacemaker's programmable parameters.

A more complete description of the pacemaker chip 12, the external programmer 24, and their operation may be found in several patents. For example, note U.S. Pat. No. 4,232,679 to Schulman, entitled "Programmable Human Tissue Stimulator"; U.S. Pat. No. 4,686,988 to Sholder, entitled "Pacemaker System and Method for Measuring and Monitoring Cardiac Activity and for Determining and Maintaining Capture"; and U.S. Pat. No. 4,809,697 to Causey et al., entitled "Interactive Programming and Diagnostic System for Use with an Implantable Pacemaker". While not disclosing the exact same pacemaker chip 12 or circuits which are used in the preferred embodiment of the present invention, these patents nonetheless disclose the primary components of a conventional pacing system and teach the basic operation thereof. U.S. Pat. No. 4,232,679; U.S. Pat. No. 4,686,988; and U.S. Pat. No. 4,809,697 are hereby incorporated herein by reference.

In the preferred embodiment, the pulse generator 14 is connected electrically to the patient's heart 30 via a lead 32. Alternatively, the pulse generator 14 may be connected to the atrium 34 and the ventricle 36 via two leads 32 and 38, respectively. These leads 32 and 38 may be either unipolar leads, bipolar leads, or other multi-pole leads, all of which are known in the art.

Figure 2A:
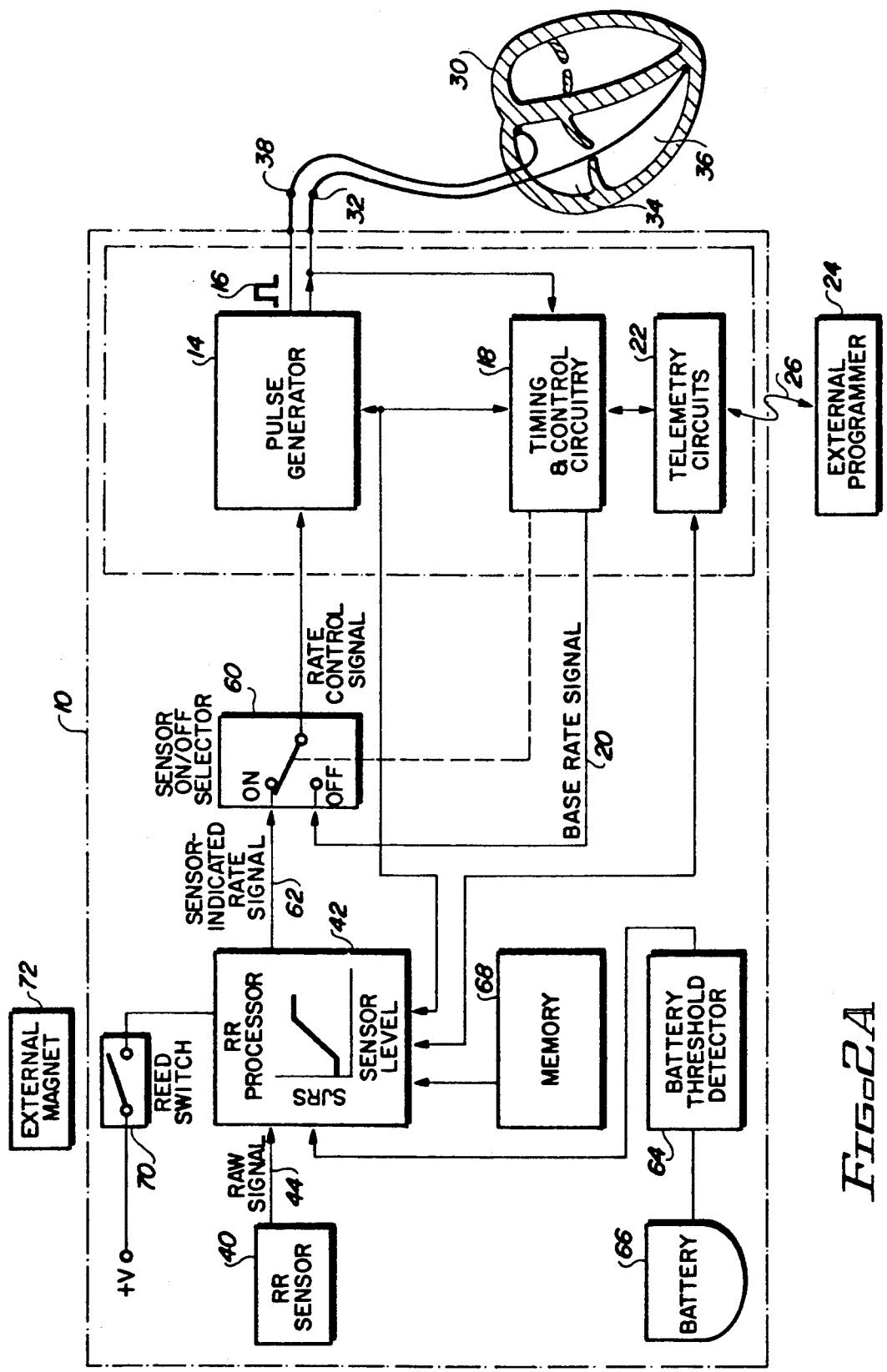
FIG. 2A is a block diagram of the present invention configured within a rate-responsive pacemaker.

The pacemaker 10 further includes a rate-responsive sensor 40 for sensing the physiological needs of the patient. In the preferred embodiment, the rate-responsive sensor 40 is a piezoelectric sensor which detects physical activity. However, the present invention is not restricted to this type of sensor and could be used with any of the known rate-responsive sensors (QT, temperature, oxygen saturation, impedance, pre-ejection period (PEP), minute volume, accelerometers, etc.). Since the invention described herein is independent of the type of sensor, hereinafter the sensor which is used to change the pacing rate shall simply be referred to as the "RR sensor". Furthermore, although the RR sensor 40 is shown in FIG. 2A as being included within the pacemaker 10, it is to be understood that the RR sensor 40 could also be included within, or coupled to, the leads 32 and 38, or otherwise placed external to the pacemaker 10.

Figure 2B:
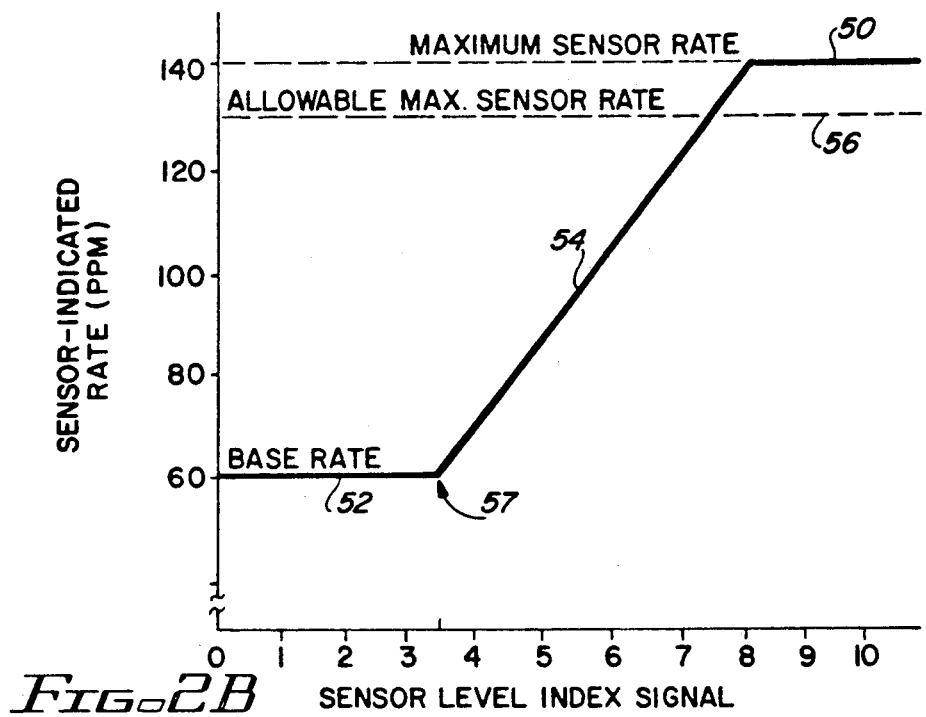
FIG. 2B is a transfer curve for the rate response processor shown in FIG. 2A.

In the preferred embodiment, the output of the RR sensor 40 is measured during each pacing cycle by the RR processor 42. Typically, the RR processor 42 includes means for converting the raw signal 44 to a sensor-indicated rate signal 62. In the preferred embodiment, the sensor-indicated rate signal 62 is based on the energy content of the raw signal 44. The conversion may be accomplished in several ways, using conventional techniques: typically by a transfer curve, look-up table (stored or programmed into the memory 68), algorithmically, or in hardware, software or a combination thereof. The preferred transfer curve is shown in FIG. 2B, wherein the physician may program a Maximum Sensor Rate (MSR) 50, a Base Rate 52 (or minimum rate), and the slope 54 and threshold 57 therebetween. Based on the energy content (x-axis), a sensor-indicated rate ma be determined.

In operation, the rate-responsive pacer may operate in either a SENSOR ON mode or a SENSOR OFF mode which can be selected by an appropriate programming signal received from the external programmer 24. A switch 60 is employed to select either the base rate signal 20 (during SENSOR OFF mode) determined by the timing and control circuitry 18 or the sensor-indicated rate signal 62 (during SENSOR ON mode) determined by the RR processor 42.

A battery threshold detector 64, connected to a battery 66, is used to detect a voltage above or below a predetermined threshold. In the preferred embodiment, the predetermined threshold is the result of an impedance level detected at RRT, however, other threshold levels may be contemplated without deviating from the basic teaching of the invention. If the pacemaker 10 is pacing at an elevated rate due to exercise or stress and the battery 66 is at or below the RRT threshold level, then the battery threshold detector 64 triggers the RR processor 42 to decrease the current pacing rate by a small amount. This decreasing of the pacemaker rate will continue until the battery 66 is above the RRT threshold, or until the current rate reaches the Base Rate. In an alternative embodiment, the decreasing of the pacemaker rate will continue until the battery 66 is above the RRT threshold, or until the current rate reaches a rate lower than the Base Rate. This reduction of pacing rate at RRT ensures that the remaining replacement time before EOL will not be rapidly used up, capture will be maintained, and that rate-responsive modes can be utilized for as long as possible.

In FIG. 3, a method for maintaining output amplitude at battery depletion is shown. A ventricular pacing cycle is initiated at 100. Following the stimulus, the battery is measured at 102. The battery voltage is compared to a predetermined threshold at step 104. If the battery voltage is above the predetermined threshold, then the RR sensor is measured and the sensor-indicated rate is determined at 120.

At 122, the sensor-indicated rate is compared to the current rate: if they are equal, no change in rate is initiated at 124 and the rate response loop ends at 125. If the sensor-indicated rate is greater than the current rate, then the current rate is compared to the (programmed) Maximum Sensor Rate at 126. If they are equal, no change in rate is initiated and the rate response loop ends at 125. If the current rate is below the (programmed) Maximum Sensor Rate, then the pacing rate is incremented by "n" steps at 128. In the preferred embodiment, "n" equal 1 step.

If the sensor-indicated rate is less than the current rate (and the battery is above the predetermined threshold) or if the battery is at or below the predetermined threshold, then the current rate is compared to the Base Rate at 130. If the current rate is equal to the Base Rate, the rate response loop ends at 125. If the current rate is above the Base Rate, then the pacing rate is decremented by "n" steps at 132. Finally, control will loop back to repeat the pacing cycle at 100, providing that rate-responsive pacing has not been turned off at 136.

In the preferred embodiment, an "allowable" maximum sensor rate (AMSR) is used to provide an intermediate rate limit based on battery measurements detected below threshold. As shown in FIG. 2B, the Allowable Maximum Sensor Rate (AMSR) 56 is adjustable between the Base Rate 52 and the (programmed) Maximum Sensor Rate (MSR) 50. Briefly, with reference to FIG. 2A, each time the battery 66 is below threshold, the RR processor 42 decreases the current rate by at least one 1 step and sets the AMSR to the new current rate. The AMSR can be stored in a counter within RR processor 42 or external to it or at a location within memory 68. The AMSR will continue to be decremented until the RR processor 42 detects at least two consecutive battery measurements above threshold or until the current rate reaches the Base Rate. When the former instance occurs, the AMSR is permitted to increment back towards the programmed Maximum Sensor Rate. These additional features enable greater rate-responsiveness for the patient by preventing a single occurrence of a low battery detection to cause the pacemaker to permanently restrict the rate.

If the current rate remains at the Base Rate for 255 beats, the rate-responsive mode will be suspended until a magnet 70 is applied to reset a reed switch 72 in the pacemaker 10 (FIG. 2A). This additional feature enables greater rate-responsiveness for the patient by preventing a single occurrence of the current rate being equal to the Base Rate from disabling the rate response mode.

In the preferred embodiment, the pacemaker 10 will not automatically return to rate-responsive pacing immediately upon reset of the reed switch 70. Instead, the pacemaker waits for a programming command from the physician via the external programmer 24. This feature allows the physician sufficient time to determine the status of the battery before re-enabling the rate-responsive mode.

Figure 4B:
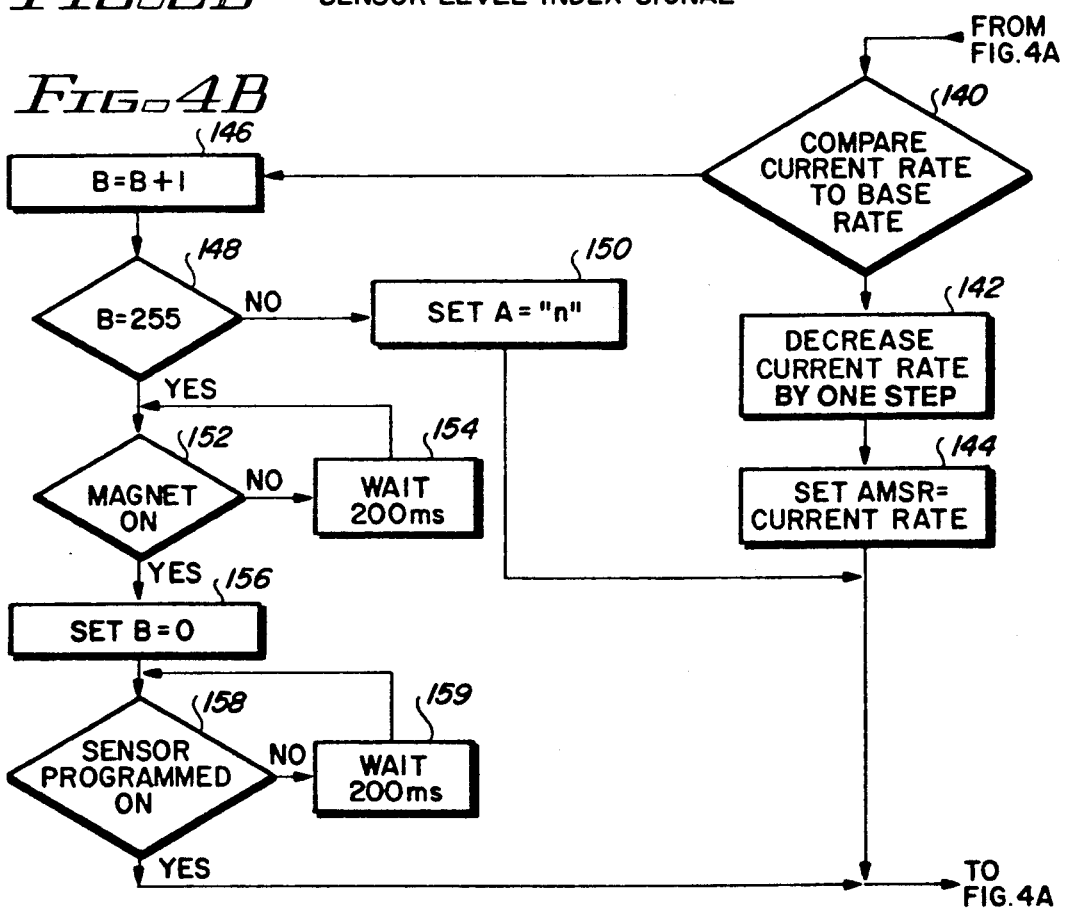
FIG. 4A and 4B show a diagram which teaches the preferred method for maintaining output amplitude at battery depletion in the rate-responsive processor shown in FIG. 2A.
Figure 4A:
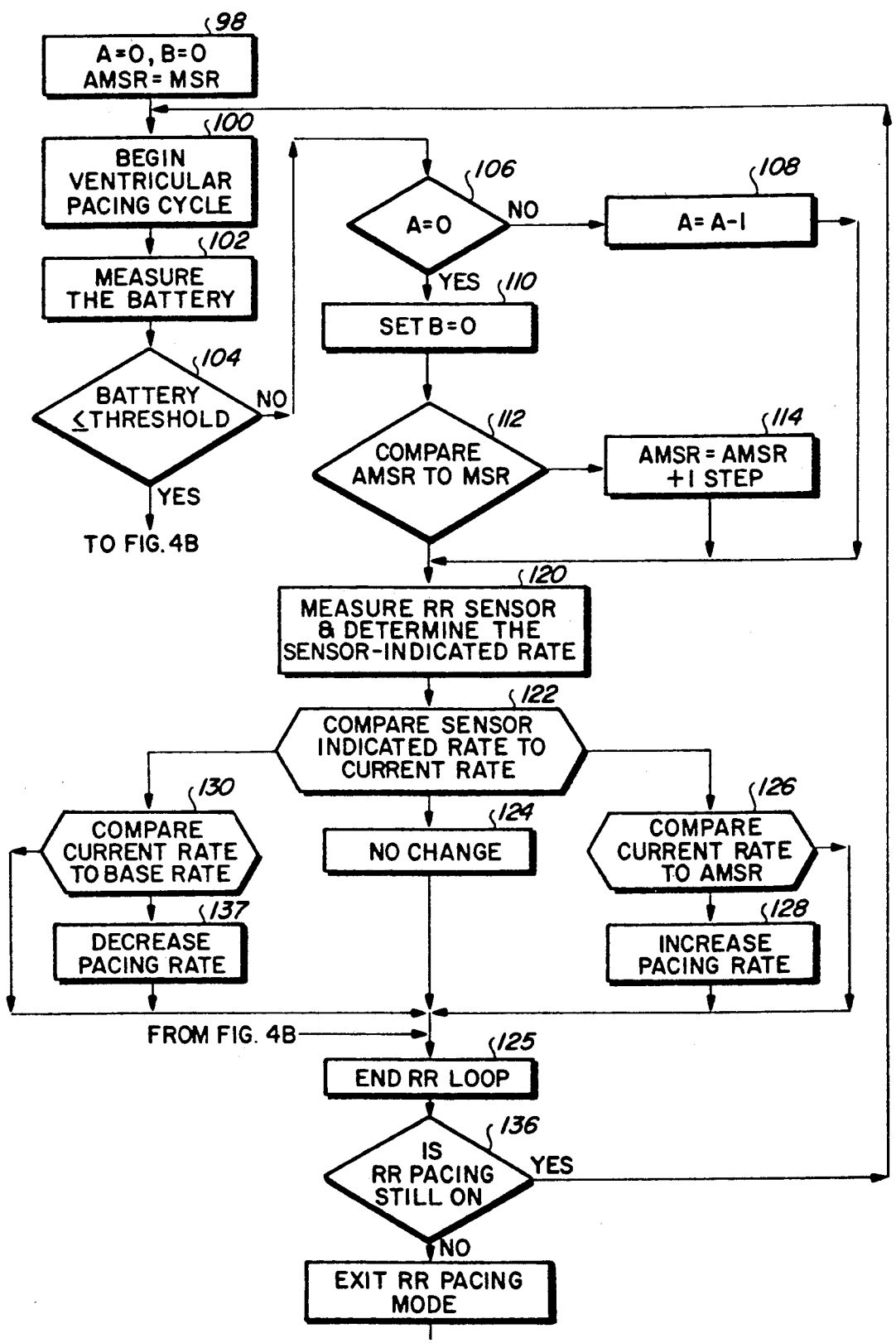

FIG. 4A and 4B describe this preferred embodiment, wherein FIG. 4A shows the steps taken when the battery is above threshold and FIG. 4B shows the steps taken when the battery is below threshold, and wherein like elements are numbered similarly as in FIG. 3.

In FIG. 4A, once RR programming has been turned ON, counters A and B are initialized to zero and the Allowable Maximum Sensor Rate (AMSR) is set equal to the programmed Maximum Sensor Rate (MSR) at step 98. A ventricular pacing cycle is initiated at 100. Following the stimulus, the battery is measured at 102. The battery voltage is compared to a predetermined threshold at step 104. If the battery voltage is above the predetermined threshold, then counter A is checked for "n" consecutive events, i.e., when the counter is zero at step 106. If the counter A is not at zero (which only occurs after at least one measurement below the predetermined threshold and is described in conjunction with FIG. 4B), then counter A is decremented at 108. If "n" consecutive events have occurred, then counter B is reset to zero at 110. (This will become meaningful later—after the complete operation of the system is described.)

At 112 the AMSR is compared to the programmed MSR. If they are equal, as is the case at BOL, the RR sensor is measured at 120 and rate-responsive pacing continues as described in FIG. 3. If they are not equal (which only occurs after at least one measurement below the predetermined threshold and is described in conjunction with FIG. 4B), the AMSR will gradually be incremented towards the MSR at step 114, that is, if the battery voltage is above the predetermined threshold for "n" consecutive cycles, the Allowable Maximum Sensor Rate is adjusted toward the (programmed) Maximum Sensor Rate.

In FIG. 4B, the steps are shown for a battery measurement which is below threshold. The current rate is compared to the Base Rate at 140. If the current rate is greater than the Base Rate, then the current rate is decremented by at least one step at 142 and the AMSR is set equal to the new current rate at 144.

If the current rate is equal to the Base Rate, then counter B is incremented at 146. If, at 148, counter B is less than 255 (or some other desired number of counts), then counter A is set to "n" at 150, thus beginning the search for "n" consecutive battery measurements above threshold. In the preferred embodiment, "n" is set to two. If counter B is equal to 255 counts, then the pacemaker waits for a magnet to be applied at steps 152 and 154, effectively suspending rate-responsive pacing. Once the magnet is applied, counter B is reset to zero at 156 and the pacemaker waits for a reprogramming signal from the external programmer at step 158 and 159.

It may therefore be appreciated by anyone skilled in the art that the invention can be extended to any pacemaker having a high current drain mode and successively lower current drain modes of operation. High current drain modes include rate-responsive pacing, automatic capture verification, automatic amplitude adjustment, automatic sensitivity adjustment, telemetry transmission of ECG data or measurements, waveform analysis, tachycardia or arrhythmia recognition, or any other features which increase microprocessor processing time. The pacemaker of the present invention would include a means for switching from a high current drain mode to a successively lower current drain mode whenever the battery threshold detector indicates that the battery voltage is below a prescribed threshold. Low current drain modes would be achieved by altering or limiting parameters such as reducing the sampling rate, pacing rate, or otherwise reducing the duty cycle of the microprocessor.

Furthermore, the present invention may incorporate a plurality of thresholds such that these high current drain features may be switched to lower current drain modes according to a predetermined priority based on basic life support and quality of life.

It may thus be appreciated from the above detailed description that the advantages of the present invention result in extending the longevity of the pacemaker while providing a higher quality of life for the patient for as long as possible, making the method of the present invention a highly desirable enhancement to implantable cardiac pacemaker therapy.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. An implantable pacemaker, comprising:
   a battery having a battery voltage which is dependent on current drain from said battery;
   a battery voltage threshold detector for detecting when said battery voltage drops below a first predetermined voltage level;
   pulse generator means for generating stimulation pulses at a variable rate up to a maximum rate-responsive pacing rate, said stimulation pulses being characterized by a plurality of variable parameters each having an initial value while said battery voltage is above said first predetermined voltage level and together defining a base current drain value, one of said parameters being said maximum rate-responsive pacing rate, said maximum rate-responsive pacing rate having a second value corresponding to a lower current drain level; and
   means for adjusting said maximum rate-responsive pacing rate to a value corresponding to a lower level of current drain when said battery voltage threshold detector detects that said battery voltage is below said first predetermined voltage level.

2. An implantable pacemaker, comprising:
   a battery having a battery voltage which is dependent on current drain from said battery;
   a battery voltage threshold detector for detecting when said battery voltage drops below a first predetermined voltage level;
   pulse generator means for generating stimulation pulses at a variable rate, said pulse generator means comprising means for operating in at least two modes of operation, a first of said modes of operation being characterized by a higher current drain value and by operation at a variable rate up to a first maximum rate, and a second of said modes of operation being characterized by a lower current drain level and by operation at a variable rate up to a maximum rate lower than said first maximum rate, said pulse generator means initially operating in said first mode of operation; and
   means for switching operation of said pulse generator to said second mode of operation when said battery voltage threshold detector detects that said battery voltage is below said first predetermined voltage level.

3. An implantable rate-responsive pacemaker, comprising:
   a battery having a battery voltage which is dependent on current drain from said battery;
   a battery voltage threshold detector for detecting when said battery voltage drops below a first predetermined voltage level;
   sensor means for sensing physiological need of a patient and for generating as an output thereof a sensor-indicated rate signal;
   a pulse generator for generating stimulation pulses according to said sensor-indicated rate signal generated by said sensor means; and
   means for decreasing said sensor-indicated rate signal when said battery voltage threshold detector detects that said battery voltage is below said first predetermined threshold voltage level.

4. An implantable rate-responsive pacemaker as defined in claim 3, wherein said sensor means comprises:
   a sensor for sensing physiological need of a patient and for generating a raw sensor signal in response thereto; and
   processing means for generating a sensor-indicated rate signal based on the raw sensor signal as sensed by the sensor.

5. An implantable rate-responsive pacemaker as defined in claim 3 additionally comprising:
   means for setting a minimum rate;
   wherein said decreasing means repeatedly decreases said sensor-indicated rate signal until either said battery voltage rises above said first threshold voltage level or said minimum rate is reached.

6. An implantable rate-responsive pacemaker as defined in claim 5, additionally comprising:
   means for setting a base rate and a maximum rate; and
   wherein said sensor-indicated rate signal has a value between said base rate and said maximum rate whenever said battery voltage is above said first threshold voltage level.

7. An implantable rate-responsive pacemaker as defined in claim 6, wherein said minimum rate is equal to said base rate.

8. An implantable rate-responsive pacemaker as defined in claim 6, wherein said minimum rate is lower than said base rate.

9. An implantable rate-responsive pacemaker as defined in claim 3 wherein said first threshold voltage level comprises:
   the voltage level corresponding to battery recommended replacement time.

10. A method of preventing rapid depletion of a battery in an implantable pacemaker, the battery having a battery voltage which is dependent on current drain from the battery, said method comprising:
    detecting when the battery voltage drops below a first predetermined voltage level;
    generating stimulation pulses at a variable rate between a base rate and a maximum pacing rate, said stimulation pulses being characterized by a plurality of variable parameters each having an initial value while said battery voltage is above said first predetermined voltage level, said parameters together defining a base current drain value, at least one of said parameters having a second value corresponding to a lower current drain level; and
    adjusting said variable rate incrementally downwardly to a value corresponding to a lower level of current drain when said battery voltage threshold detector detects that said battery voltage is below said first predetermined voltage level.

11. A method of preventing rapid depletion of a battery in an implantable pacemaker, the battery having a battery voltage which is dependent on current drain from the battery, said method comprising:
    detecting when the battery voltage drops below a first predetermined voltage level;
    generating stimulation pulses at a variable rate between a base rate and a first maximum pacing rate with a pulse generator means operating in at least two modes of operation, a first of said modes of operation being characterized by a higher current drain value and by operation at a variable rate up to said first maximum pacing rate, and a second of said modes of operation being characterized by a lower current drain level and by operation at a variable rate up to a maximum rate lower than said first maximum pacing rate, said pulse generator means initially operating in said first mode of operation; and switching operation of said pulse generator to said second mode of operation when said battery voltage threshold detector detects that said battery voltage is below said first predetermined voltage level.

12. A method of preventing rapid depletion of a battery in an implantable pacemaker, the battery having a battery voltage which is dependent on current drain from the battery, said method comprising:

detecting when the battery voltage drops below a first predetermined voltage level;

sensing physiological need of a patient and generating in response thereto a sensor-indicated rate signal;

generating stimulation pulses according to said sensor-indicated rate signal; and decreasing said sensor-indicated rate signal when said battery voltage is detected below said first predetermined threshold voltage level.

13. A method as defined in claim 12, wherein sensing step comprises:

sensing physiological need of a patient and generating a raw sensor signal in response thereto; and generating said sensor-indicated rate signal based on said raw sensor signal.

14. A method as defined in claim 12, additionally comprising:

setting a minimum rate; wherein said decreasing means repeatedly decreases said sensor-indicated rate signal until either said battery voltage rises above said first threshold voltage level or said minimum rate is reached.

15. A method as defined in claim 14, additionally comprising:

setting a base rate and a maximum rate; wherein said sensor-indicated rate signal has a value between said base rate and said maximum rate whenever said battery voltage is above said first threshold voltage level.

16. A method as defined in claim 15, additionally comprising:

setting said minimum rate equal to said base rate.

17. A method as defined in claim 15, additionally comprising:

setting said minimum rate lower than said base rate.

18. A method as defined in claim 12, additionally comprising:

setting said first threshold voltage level to the voltage level corresponding to battery recommended replacement time.

19. A method of preventing rapid depletion of a battery in an implantable pacemaker, the battery having a battery voltage which is dependent on current drain from the battery, said method comprising:

detecting when the battery voltage drops below a first predetermined voltage level;

sensing physiological need of a patient with a sensor and generating a raw sensor signal with said sensor in response to sensed physiological need;

generating a sensor-indicated rate signal based on the raw sensor signal as sensed by the sensor;

generating a sensor-indicted rate signal based on said raw sensor signal;

generating stimulation pulses according to said sensor-indicated rate signal; and decreasing said sensor-indicated rate signal when said battery voltage is detected below said first predetermined threshold voltage level.

20. An implantable pacemaker, comprising:

a battery having a battery voltage which is dependent on current drain from said battery;

a battery voltage threshold detector for detecting when said battery voltage drops below a first predetermined voltage level;

pulse generator means for generating stimulation pulses at a variable rate equal to a base pacing rate plus a sensor-indicated rate differential, said stimulation pulses being characterized by a plurality of variable parameters each having an initial value while said battery voltage is above said first predetermined voltage level and together defining a base current drain value, one of said parameters being said sensor-indicated rate differential, said sensor-indicated rate differential having a second value corresponding to a lower current drain level; and means for adjusting said sensor-indicated rate differential to a value corresponding to a lower level of current drain when said battery voltage threshold detector detects that said battery voltage is below said first predetermined voltage level.

21. A method of preventing rapid depletion of a battery in an implantable pacemaker, the battery having a battery voltage which is dependent on current drain from the battery, said method comprising:

detecting when the battery voltage drops below a first predetermined voltage level;

generating stimulation pulses at a variable rate up to a maximum rate-responsive pacing rate, said stimulation pulses being characterized by a plurality of variable parameters each having an initial value while said battery voltage is above said first predetermined voltage level, said parameters together defining a base current drain value, one of said parameters being said maximum rate-responsive pacing rate, said maximum rate-responsive pacing rate having a second value corresponding to a lower current drain level; and adjusting said maximum rate-responsive pacing rate to a value corresponding to a lower level of current drain when said battery voltage threshold detector detects that said battery voltage is below said first predetermined voltage level.

22. A method of preventing rapid depletion of a battery in an implantable pacemaker, the battery having a battery voltage which is dependent on current drain from the battery, said method comprising:

detecting when the battery voltage drops below a first predetermined voltage level;

generating stimulation pulses at a variable rate equal to a base pacing rate plus a sensor-indicated rate differential, said stimulation pulses being characterized by a plurality of variable parameters each having an initial value while said battery voltage is above said first predetermined voltage level, said parameters together defining a base current drain value, one of said parameters being said sensor-indicated rate differential, said sensor-indicated rate differential having a second value corresponding to a lower current drain level; and adjusting said sensor-indicated rate differential to a value corresponding to a lower level of current drain when said battery voltage threshold detector detects that said battery voltage is below said first predetermined voltage level.

* * * * *